United States Patent [19]

Blank et al.

[11] 4,407,762
[45] Oct. 4, 1983

[54] PROCESS FOR THE ISOLATION OF 1-NAPHTHYLAMINE-4,8-DISULPHONIC ACID

[75] Inventors: Heinz U. Blank; Horst Behre, both of Odenthal; Hans W. Linden, Leverkusen; Werner Mentzel, Cologne, all of Fed. Rep. of Germany

[73] Assignee: Bayer Aktiengesellschaft, Leverkusen, Fed. Rep. of Germany

[21] Appl. No.: 410,746

[22] Filed: Aug. 23, 1982

[30] Foreign Application Priority Data

Sep. 7, 1981 [DE] Fed. Rep. of Germany ....... 3135391

[51] Int. Cl.³ .......................................... C07C 143/60
[52] U.S. Cl. .................................................. 260/508
[58] Field of Search ........................................ 260/508

[56] References Cited

U.S. PATENT DOCUMENTS 3,979,445 9/1976 Ross et al. ........................... 260/508
4,199,529 4/1980 Bonath et al. ....................... 260/508
4,348,336 9/1982 Blank et al. ......................... 260/508

*Primary Examiner*—Alan Siegel
*Attorney, Agent, or Firm*—Sprung, Horn, Kramer & Woods

[57] ABSTRACT

Process for the isolation of 1-naphthylamine-4,8-disulphonic acid from sulphonation mixtures containing it according to which process the sulphonation mixture is introduced into preheated water in such a manner that, at the start of crystallization, a temperature of at least 100° C. is reached and the 1-naphthylamine-4,8-disulphonic acid is separated from the mother liquor at a temperature not higher than 70° C. The process is applied particularly advantageously for the isolation of 1-naphthylamine-4,8-disulphonic acid from sulphonation mixtures which have been obtained by introducing in turns alkali metal sulphate, 1-naphthylamine-8-sulphonic acid and $SO_3$ into sulphuric acid which has been introduced initially, a total of 1.5 to 3 mols of $SO_3$ and 0.6 to 1.5 mols of alkali metal sulphate being employed per mol of 1-naphthylamine-8-sulphonic acid.

9 Claims, No Drawings

PROCESS FOR THE ISOLATION OF 1-NAPHTHYLAMINE-4,8-DISULPHONIC ACID

The invention relates to a process for the isolation of 1-naphthylamine-4,8-disulphonic acid from sulphonation mixtures containing it by introduction into preheated water.

1-naphthylamine-4,8-disulphonic acid is an important intermediate product for the preparation of dyestuffs.

A number of processes for the preparation of 1-naphthylamine-4,8-disulphonic acid have already been disclosed. Thus, for example, a process is described in French Patent Specification No. 1,490,508 according to which 1-naphthylamine-8-sulphonic acid is sulphonated with manganese dioxide and sodium hydrogen sulphite in alcoholic-aqueous solution. However, this process has the disadvantage that expensive manganese dioxide is used, a poor space-time yield is obtained and large amounts of salt-containing mother liquor results. In addition, for the working up, separation off of the excess manganese dioxide and complete removal of sulphur dioxide by boiling are necessary. Thus this process is not suitable for conversion to the industrial scale.

Other processes start from naphthalene, which is sulphonated to naphthalene-1,5-disulphonic acid, is nitrated in the 4-position and finally is reduced to 1-naphthylamine-4,8-disulphonic acid. Such processes are described, for example, in Beilstein, Hauptwerk, Volume XIV, page 787, Ullmanns Enzyklopädie der technischen Chemie [Ullmann's Encyclopaedia of Industrial Chemistry], 3rd edition, Volume 12, page 629 (1960) and in German Patent Specification 45,776, cited in Friedländer, Volume 2, page 253. The yields of disulphonic acid isolated are only a little over 30% of the theoretical yield.

The processes in which the sulphonation of 1-naphthylamine-8-sulphonic acid is carried out with oleum are of industrial interest. Such processes are described, for example, in Beilstein, Hauptwerk, Volume XIV, page 787, German Patent Specification No. 40,571, cited in Friedländer, Volume 1, page 394 and in the Office Techn. Services Reports 74,197, cited in Ullmanns Enzyklopädie der technischen Chemie [Ullmann's Encyclopaedia of Industrial Chemistry], 3rd edition, Volume 12, page 629 (1960).

According to the data in German Patent Specification No. 40,571, 1-naphthylamine-8-sulphonic acid should be sulphonated to 1-naphthylamine-4,8-disulphonic acid by introduction into 10% strength oleum, avoiding heating, and subsequent heating on the water bath until a sample is completely soluble in water. In this process, large amounts of isomeric disulphonic acids and higher sulphonated products are formed, which necessitate the isolation of pure 1-naphthylamine-4,8-disulphonic acid by an expensive procedure of dissolving and allowing to crystallise.

According to the Office Techn. Services Reports 74,197, 1-naphthylamine-8-sulphonic acid is sulphonated with 65% strength oleum in the presence of anhydrous sodium sulphate in 100% strength sulphuric acid as the reaction medium. In this process, sodium sulphate, 1-naphthylamine-8-sulphonic acid and about one half of the total amount of oleum necessary are introduced in 6 portions in turns into the sulphuric acid at 20° C. Finally, the remaining oleum is added and the mixture is stirred at 20° to 30° C. for about 40 hours. The molar ratio $SO_3:Na_2SO_4:$1-naphthylamine-8-sulphonic acid is 3.3:0.5:1 in this process. The sulphonation mixture obtained is introduced under pressure into water and the 1-naphthylamine-4,8-disulphonic acid is salted out with sodium chloride. The product is filtered off by suction and the press cake is dissolved and allowed to crystallise. The yield is reported to be 82% of the theoretical yield.

However, following this procedure, isolated yields of less than 60% of the theoretical yield were obtained even when a procedure of dissolution and crystallisation is omitted. The disadvantages of the abovementioned process are the poor yield, the large amounts of sodium chloride necessary for salting out, the unsatisfactory behaviour of the crude product on filtration and the necessity for the crude material to be dissolved and allowed to crystallise in order to obtain a pure and salt-free product. In addition, relatively large amounts of by-products occur during sulphonation, such as 1-naphthylamine-3,8-disulphonic acid, 1-naphthylamine-6,8-disulphonic acid and 1,8-naphthalenesultam-2,4-disulphonic acid, which all remain to some extent in the desired 1-naphthylamine-4,8-disulphonic acid after isolation.

A process for the isolation of 1-naphthylamine-4,8-disulphonic acid from sulphonation mixtures containing it by introduction into water has now been found, which is characterised in that the sulphonation mixture containing 1-naphthylamine-4,8-disulphonic acid is introduced, in the presence of at least one equivalent of alkali metal ions, into water, if appropriate preheated, so that a temperature of at least 100° C. is reached at the start of crystallisation, and the separation of 1-naphthylamine-4,8-disulphonic acid from the mother liquor is carried out at a temperature not higher than 70° C.

The sulphonation mixture can be introduced into water at room temperature or into preheated water, preferably into preheated water.

Examples of the temperatures of the preheated water which may be mentioned are 40° C. to the boiling point at normal pressure, preferably at least 70° C., particularly preferably at least 80° C.

The sulphonation mixture is introduced into this preheated water so that a temperature at the start of crystallisation of 1-naphthylamine-4,8-disulphonic acid is reached which is at least 100° C., for example, 100° C. to a little below the boiling point of the suspension being formed. An advantageous variant of the introduction of the sulphonation mixture into the preheated water consists of heating only a part of this water, for example 20 to 50% of the total amount, initially introducing this and then simultaneously introducing the sulphonation mixture, and the remaining water which has not been preheated, into the preheated part of the water.

The total amount of water with which the sulphonation mixture is combined, is set, according to the invention, such that the concentration of sulphuric acid in the mother liquor of the suspension being produced is about 10 to 70% by weight, preferably 30 to 60% by weight.

The 1-naphthylamine-4,8-disulphonic acid is separated from the suspension being produced by filtration, decantation or centrifugation, preferably by filtration. Before starting the isolation, for example by filtration, the suspension is brought to a temperature not exceeding 70° C. The 1-naphthylamine-4,8-disulphonic acid is filtered off in a preferred manner at a temperature of 10° to 30° C.

The process according to the invention is applicable to the isolation of 1-naphthylamine-4,8-disulphonic acid from all sulphonation mixtures in which sulphonation is carried out with sulphuric acid and sulphur trioxide under reaction conditions which may otherwise vary, when at least one equivalent of alkali metal ions is present during the aqueous work-up of the sulphonation mixtures. The 1-naphthylamine-4,8-disulphonic acid is isolated as an acid monoalkali metal salt in the process according to the invention.

Examples of alkali metal ions which may be mentioned are lithium, sodium, potassium, rubidium or caesium ions or the ammonium ions. The sodium, potassium or ammonium ions may be mentioned in preference and sodium ions may be mentioned particularly preferably. Accordingly the 1-naphthylamine-4,8-disulphonic acid is isolated, for example, as the monosodium, monopotassium or monoammonium salt.

These alkali metal ions can, for example, be present in the aqueous suspension in the form of the relevant sulphates or hydrogen sulphates. The sulphates of these alkali metal ions are used in a preferred manner.

The alkali metal ions are present in an amount of at least 1 equivalent per mol of 1-naphthylamine-4,8-disulphonic acid, for example in an amount of 1 to 10 equivalents, preferably 1.1 to 6 equivalents, particularly preferably 1.2 to 4 equivalents. It is inconsequential for the process according to the invention whether the alkali metal ions reach the suspension in the form of the abovementioned salts with the sulphonation mixture or are added to this suspension independently of the sulphonation mixture. The alkali metal salts preferably reach the suspension with the sulphonation mixture.

Thus, in a preferred manner, sulphonation mixtures are employed in the process according to the invention, which is carried out in the presence of at least 1 equivalent of alkali metal ions per mol of 1-naphthylamine-8-sulphonic acid to be sulphonated. Such a sulphonation can be carried out, for example, in a manner such that one or more alkali metal and/or ammonium salts, preferably the sulphates, 1-naphthylamine-8-sulphonic acid, and if necessary, diluted $SO_3$ are introduced in turns into the sulphuric acid which has been initially introduced.

It has now been found that particularly favourable results are obtained in respect of the sulphonation conversion, the selectivity to the desired 1-naphthylamine-4,8-disulphonic acid and the subsequent aqueous work-up, when the total amount of substances introduced in turn as described, for the sulphonation in $H_2SO_4$ as the reaction medium, is 1.5 to 3 mols of $SO_3$ and 0.6 to 1.5 mols of alkali metal sulphate per mol of 1-naphthylamine-8-sulphonic acid.

Thus the invention relates, in a preferred manner, to a process for the isolation of 1-naphthylamine-4,8-disulphonic acid from sulphonation mixtures containing this acid which process is characterised in that the sulphonation mixtures used are those which are obtained by the known sulphonation in sulphuric acid by introducing in turns $SO_3$, alkali metal sulphate and 1-naphthylamine-8-sulphonic acid while using a total of 1.5 to 3 mols of $SO_3$ and 0.6 to 1.5 mols of alkali metal sulphate per mol of 1-naphthylamine-8-sulphonic acid and in that the sulphonation mixtures which have reacted to completion are introduced in the described manner into water which has if necessary, been preheated, so that a temperature of at least 100° C. is reached at the start of crystallisation, and the separation of 1-naphthylamine-4,8-disulphonic acid from the mother liquor is carried out at a temperature not exceeding 70° C.

$SO_3$ may be applied as such or in form of solutions in sulphuric acid. Such solutions of $SO_3$ in sulphuric acid are known under the name oleum. Oleum may contain various contents of $SO_3$. In accordance with the invention, an oleum with 50 to 80% by weight of $SO_3$, related to the total weight of the oleum, is preferably employed.

The total amount of $SO_3$ is 1.5 to 3 mols per mol of 1-naphthylamine-8-sulphonic acid. The $SO_3$, optionally in the form of oleum, can here be used completely in the form of the introduction in turn of all the starting materials. However, it can be advantageous to introduce only about one half of the $SO_3$ or oleum in turn with the other materials used, the other half of the $SO_3$ or oleum being metered in after the complete introduction of the other materials used, for example 0.5 to 3 hours thereafter. 2.5 to 3 mols of $SO_3$ are preferably employed per mol of 1-naphthylamine-8-sulphonic acid.

In addition, 0.6 to 1.5 mols, preferably 0.75 to 1.0 mol, of one or more alkali metal and/or ammonium sulphates are employed according to the invention per mol of 1-naphthylamine-8-sulphonic acid. The alkali metal and/or ammonium sulphate can be employed in turn together with the other starting materals as described above. However, it is equally possible to introduce initially the total amount of alkali metal and/or ammonium sulphate into the reaction medium and only then introduce the other starting materials of the process in turn.

The sulphonation of 1-naphthylamine-8-sulphonic acid is carried out in anhydrous sulphuric acid as reaction medium. The amount of sulphuric acid is 5 to 7 mols of $H_2SO_4$ per mol of 1-naphthylamine-8-sulphonic acid. If sulphuric acid containing water is used to dissolve or suspend, and/or 1-naphthylamine-8-sulphonic acid is employed which is not dry, but moist, sulphur trioxide, if appropriate in the form of oleum, should be added for the sulphonation in an amount exceeding that mentioned above of 1.5 to 3 mols per mol of 1-naphthylamine-8-sulphonic acid as is necessary to bind the water introduced with the reagents with the formation of sulphuric acid.

The introduction of the starting materials in turns and the continuation of the sulphonation is carried out, for example, at a temperature of 10° to 40° C., preferably at 25° to 35° C. After addition of all starting materials for the process is complete, if appropriate also after supplementary addition of a part of the oleum, the reaction mixture is allowed to react to completion with stirring at the temperature given. The subsequent reaction time is about 16 to about 40 hours, preferably 20 to 36 hours.

The suspensions obtained according to the invention containing 1-naphthylamine-4,8-disulphonic acid are distinguished by being easily filtered. The 1-naphthylamine-4,8-disulphonic acid prepared according to the invention has a high purity of at least 97%, preferably at least 98.5%.

EXAMPLE 1

630 g of 100% strength sulphuric acid are initially introduced into a reaction vessel provided with a stirrer, dropping funnel, internal thermometer and drying tube. Then 26.7 g (0.1875 mol) of anhydrous sodium sulphate, 57 g (0.25 mol) of 97.8% pure 1-naphthylamine-8-sulphonic acid and 46.2 g of 65% oleum (=0.375 mol of $SO_3$) at a time are introduced four times in this sequence at 20° to 30° C. with cooling. The introduction of each portion of sodium sulphate, 1-naphthylamine-8-sulphonic acid and oleum should be carried out in 15 to 20 minutes. The mixture is then stirred at 30° C. for 1 hour and then a further 123.1 g of 65% oleum (=1.0 mol of $SO_3$) is added at 30° C. in 30 minutes; initially, cooling is still necessary, but slight heating is subsequently needed. The mixture is then stirred for 36 hours at 30° C.

The final sulphonation mixture is introduced in about 1 hour into 1,360 g of water which has been initially introduced and has a temperature of 80° C. During this introduction the temperature rises to about 105° C. After about ⅓ of the sulphonation mixture has been introduced, the 1-naphthylamine-4,8-disulphonic acid starts to crystallise; the temperature at this point in time is 105° C. After introduction of the sulphonation mixture is complete, the mixture is cooled with stirring to 20° to 25° C. in about 6 hours. The suspension is filtered and washed twice with 100 ml of ice-water each time to remove sulphuric acid and is sucked dry.

274.3 g of product are obtained.

High pressure liquid chromatography of the isolated product gave the following composition:

| | |
|---|---|
| 1-naphthylamine-8-sulphonic acid | 0.2% by weight |
| 1-naphthylamine-3,8-disulphonic acid | 0.5% by weight |
| 1-naphthylamine-4,8-disulphonic acid | 90.4% by weight |
| 1-naphthylamine-6,8-disulphonic acid | 0.1% by weight |
| 1,8-naphthalenesultam-2,4-disulphonic acid | trace |
| remainder up to 100% | water |

The yield of pure 1-naphthylamine-4,8-disulphonic acid (molecular weight 303) is 248 g (=81.8% of the theoretical yield, related to the 1-naphthylamine-8-sulphonic acid used). The disulphonic acid is in the form of an acid monosodium salt.

EXAMPLE 2

1,260 g of 100% strength sulphuric acid are initially introduced into an apparatus as described in Example 1. Then 53.3 g (0.375 mol) of anhydrous sodium sulphate, 114.1 g (0.5 mol) of 97.8% pure 1-naphthylamine-8-sulphonic acid and 92.3 g of 65% oleum (=0.75 mol of $SO_3$) are each introduced four times in this sequence at 20° to 30° C. with cooling. The introduction of each portion of sodium sulphate, 1-naphthylamine-8-sulphonic acid and oleum should be carried out in 15 to 20 minutes. The mixture is then stirred at 30° C. for 1 hour and then a further 369.3 g of 65% oleum (=3.0 mol of $SO_3$) are added dropwise in 30 minutes at 20° C. The mixture is subsequently stirred at 30° C. for 24 hours; initially, cooling is still necessary, but subsequently slight heating is needed.

500 g of water are heated to boiling in a stirred apparatus, and 2,400 g of water of room temperature and the abovementioned sulphonation mixture are added simultaneously with stirring in about 1 hour. The diluted aqueous solution or suspension of the sulphonation mixture is maintained during the addition at a temperature of 103° to 105° C. by warming. After introduction of the sulphonation mixture is complete, the mixture is cooled with stirring from 103°–105° C. to 20°–25° C. in about 6 hours. The suspension is filtered and washed twice with 200 ml of ice-water each time to remove sulphuric acid and sucked dry.

545 g of air-dried product are obtained.

High pressure liquid chromatography of the isolated product gave the following composition:

| | |
|---|---|
| 1-naphthylamine-8-sulphonic acid | 0.3% by weight |
| 1-naphthylamine-3,8-disulphonic acid | 0.4% by weight |
| 1-naphthylamine-4,8-disulphonic acid | 86.1% by weight |
| 1-naphthylamine-6,8-disulphonic acid | 0.3% by weight |
| 1,8-naphthalenesultam-2,4-disulphonic acid | trace |
| remainder up to 100% | water |

The yield of pure 1-naphthylamine-4,8-disulphonic acid (molecular weight 303) is 469.2 g (=77.4% of the theoretical yield, related to 1-naphthylamine-8-sulphonic acid employed). The disulphonic acid is in the form of an acid monosodium salt.

EXAMPLES 3 TO 9

Sulphonation is carried out as described in Example 1, but other molar ratios of sulphur trioxide:sodium sulphate:1-naphthylamine-8-sulphonic acid, other reaction temperatures and subsequent times of stirring are employed.

The results obtained in these sulphonation processes are compiled in Table I below. The composition of the sulphonation mixtures was determined by means of high pressure liquid chromatography.

TABLE I

| | Sulphonation conditions | | | Composition of the sulphonation mixture in [mol %] | | | | | |
|---|---|---|---|---|---|---|---|---|---|
| Example Number | Molar ratio $SO_3$:$Na_2SO_4$: 1-$NH_2$—8-S | React. Temp. [°C.] | Subsequent stirring time [h] | 1-$NH_2$—8 | 1-$NH_2$—3,8 | 1-$NH_2$—4,8 | 1-$NH_2$—6,8 | 1-naph-thalene-sultam-2,4 | $\Sigma$ |
| 3 | 3.0:0.54:1 | 20 | 36 | 0.8 | 3.6 | 75.5 | 10.0 | 2.3 | 92.2 |
| 4 | 3.0:0.75:1 | 30 | 24 | <0.5 | 2.7 | 81.0 | 6.9 | 4.6 | 95.7 |
| 5 | 3.0:1.0:1 | 35 | 32 | 1.5 | 2.4 | 75.3 | 6.1 | 8.9 | 94.2 |
| 6 | 2.5:0.54:1 | 30 | 36 | 1.0 | 2.7 | 78.3 | 7.1 | 2.3 | 91.9 |
| 7 | 2.5:0.75:1 | 30 | 36 | 0.6 | 2.3 | 84.6 | 6.1 | 5.4 | 98.0 |
| 8 | 2.5:0.75:1 | 35 | 32 | <0.5 | 2.1 | 80.9 | 5.5 | 8.1 | 96.6 |
| 9 | 2.0:0.5:1 | 40 | 36 | <0.5 | 2.1 | 73.8 | 5.3 | 12.3 | 93.5 |

EXAMPLES 10 TO 18

Sulphonation was carried out as described in Example 2, but the batch size was only half as large. For the work-up, the total amount of water is intially introduced and heated to 80° C. The sulphonation mixture is introduced with stirring, during which the temperature rises to 105° C. The temperature of the diluted aqueous solution or suspension of the reaction mixture is maintained at about 105° C. until introduction of the sulphonation mixture is complete. The mixture was then cooled with stirring.

As can be seen from the following Table II, various amounts of water were initially introduced for the work-up and various concentrations of sulphuric acid in the aqueous solutions or suspensions of the sulphonation mixtures were obtained in this manner. In addition, the mono Na salt of 1-naphthylamine-4,8-disulphonic acid which crystallised out is filtered off with suction at various temperatures and then washed twice with 100 ml of ice-water each time to remove sulphuric acid.

The composition of the mono Na salt of 1-naphthylamine-4,8-disulphonic acid isolated under various conditions was found by means of high pressure liquid chromatography.

EXAMPLE 20

(Sulphonation in accordance with Office Techn. Reports 74,197).

510 g of 100% strength sulphuric acid are initially introduced into an apparatus described in Example 1. Then 17.7 g of anhydrous sodium sulphate, 57.1 g of 97.8% pure 1-naphthylamine-8-sulphonic acid and 31.7

TABLE II

| | Work-up | | | | Composition of the solid material [in % by weight][1] | | | | Yield 1-naphthyl-amine-4,8-disulphonic acid [% of theory] |
|---|---|---|---|---|---|---|---|---|---|
| Example Number | Amount of water initially introduced [g] | % by weight of H$_2$SO$_4$ in the mother liquor | Filtration temp. [°C.] | Amount weighed [g] | 1-naphthyl-amine-8-sulphonic acid | 1-naphthyl-amine-3,8-disulphonic acid | 1-naphthyl-amine-4,8-disulphonic acid | 1-naphthyl-amine-6,8-disulphonic acid | |
| 10 | 1,450 | 40 | 20 | 267.0 | 0.2 | 0.5 | 88.0 | 0.3 | 77.5 |
| 11 | 1,450 | 40 | 40 | 259.7 | <0.1 | 0.4 | 87.8 | 0.3 | 75.1 |
| 12 | 1,450 | 40 | 60 | 260.0 | <0.1 | 0.4 | 87.2 | 0.3 | 74.8 |
| 13 | 967 | 50 | 20 | 249.5 | 0.2 | 0.6 | 92.0 | 0.2 | 75.7 |
| 14 | 967 | 50 | 40 | 262.9 | 0.2 | 0.6 | 82.6 | 0.2 | 71.6 |
| 15 | 967 | 50 | 60 | 250.5 | 0.2 | 0.6 | 85.3 | 0.2 | 70.5 |
| 16 | 645 | 60 | 20 | 267.0 | 0.2 | 0.8 | 85.1 | 0.3 | 74.9 |
| 17 | 645 | 60 | 40 | 257.7 | 0.2 | 0.7 | 84.7 | 0.3 | 72.0 |
| 18 | 645 | 60 | 60 | 239.2 | 0.2 | 0.7 | 82.6 | 0.4 | 65.1 |

[1]The 1,8-naphthalenesultam-2,4-disulphonic acid is present in the crystalline product only in traces.

EXAMPLE 19

1,260 g of 100% strength sulphuric acid and 198.2 g (1.5 mol) of anhydrous ammonium sulphate are initially introduced into an apparatus described in Example 1. Then 114.1 g (0.5 mol) of 97.8pure 1-naphthylamine-8-sulphonic acid and 92.3 g of 65% oleum (=0.75 mol of SO$_3$) are each introduced four times in this sequence at 20° to 30° C. with cooling. The introduction of each portion of 1-naphthylamine-8-sulphonic acid and oleum should be carried out in about 15 minutes. The mixture is subsequently stirred at 30° C. for 1 hour and then a further 369.3 g of 65% oleum (=3.0 mol of SO$_3$) are added dropwise in 30 minutes at 30° C. The mixture is then stirred for 24 hours at 30° C.

2,900 g of water at 80° C. are initially introduced into a stirring apparatus and the sulphonation mixture is introduced in about 1 hour with stirring. The temperature of the diluted aqueous solution or suspension of the sulphonation mixture is raised to and maintained at about 105° C. by warming. Then, in about 6 hours, the temperature is reduced from 105° C. to 20°–25° C. The suspension is filtered and washed twice with 150 ml of ice-water each time to remove sulphuric acid and sucked dry.

501 g of air-dried product are obtained.

High pressure liquid chromatography of the isolated product gave the following composition:

| | |
|---|---|
| 1-naphthylamine-8-sulphonic acid | 0.1% by weight |
| 1-naphthylamine-3,8-disulphonic acid | 0.5% by weight |
| 1-naphthylamine-4,8-disulphonic acid | 87.5% by weight |
| 1-naphthylamine-6,8-disulphonic acid | 0.1% by weight |
| 1,8-naphthalenesultam-2,4-disulphonic acid | trace |
| remainder up to 100% | water |

The yield of pure 1-naphthylamine-4,8-disulphonic acid (molecular weight 303) is 438.4 g (=72.3% of the theoretical yield, related to 1-naphthylamine-8-sulphonic acid employed). The disulphonic acid is in the form of an acid monoammonium salt.

g of 65% oleum are added one after the other at 20° to 30° C. The same amounts are introduced once more in the stated sequence. Then 8.9 g of anhydrous sodium sulphate, 28.5 g of 97.8% pure 1-naphthylamine-8-sulphonic acid and 31.7 g of 65% oleum are each introduced four times. Then a total of 71 g (0.5 mol) of anhydrous sodium sulphate, 228.2 g (1 mol) of 97.8% pure 1-naphthylamine-8-sulphonic acid and 190.2 g of 65% oleum (=1.55 mol of SO$_3$) are introduced. Finally, another 215.4 g of 65% oleum (=1.75 mol of SO$_3$) are added as a supplement. The sulphonation mixture is then stirred for about 40 hours at 20° to 30° C.

The yield of 1-naphthylamine-4,8-disulphonic acid determined by high pressure liquid chromatography of the finished sulphonation product is 64.4% of the theoretical yield, related to 1-naphthylamine-8-sulphonic acid employed.

High pressure liquid chromatography of the sulphonation mixture gave the following composition:

| | |
|---|---|
| 1-naphthylamine-8-sulphonic acid | 0.15% by weight (= 0.8 mol %) |
| 1-naphthylamine-3,8-disulphonic acid | 1.17% by weight (= 4.7 mol %) |
| 1-naphthylamine-4,8-disulphonic acid | 16.07% by weight (= 64.4 mol %) |
| 1-naphthylamine-6,8-disulphonic acid | 2.97% by weight (= 11.9 mol %) |
| 1,8-naphthalenesultam-2,4-disulphonic acid | 0.36% by weight (= 1.2 mol %) |
| remainder up to 100% | sulphuric acid, sulphur trioxide, sodium sulphate, undefined compounds |

The sulphonation mixture thus prepared is added to 2,110 g of water, during which the solution heats up to about 90° C. The 1-naphthylamine-4,8-disulphonic acid is salted out with 169 g of sodium chloride. After cooling down, filtration is carried out and the crude acid is washed with a little ice-water to remove sulphuric acid. The product is dried in a vacuum drying oven at 70° C. for 24 hours. 316 g of product are obtained.

High pressure liquid chromatography of the isolated product gave the following composition:

| | |
|---|---|
| 1-naphthylamine-8-sulphonic acid | 0.10% by weight |
| 1-naphthylamine-3,8-disulphonic acid | 1.29% by weight |
| 1-naphthylamine-4,8-disulphonic acid | 56.40% by weight |
| 1-naphthylamine-6,8-disulphonic acid | 1.54% by weight |
| 1,8-naphthalenesultam-2,4-disulphonic acid | 0.19% by weight |
| remainder up to 100% | sodium chloride, sodium sulphate and water |

The yield of pure 1-naphthylamine-4,8-disulphonic acid (molecular weight 303) is 178.2 g (=58.8% of the theoretical yield, related to 1-naphthylamine-8-sulphonic acid employed). The disulphonic acid is in the form of an acid monosodium salt.

What is claimed is:

1. In the process for the isolation of 1-naphthylamine-4,8-disulphonic acid from sulphonation mixtures containing it by introducing these sulphonation mixtures into water, the improvement comprising introducing the sulphonation mixture containing 1-naphthylamine-4,8-disulphonic acid, in the presence of at least one equivalent of alkali metal ions, into water, if appropriate preheated, so that a temperature of at least 100° C. is reached at the start of crystallisation of the 1-naphthylamine-4,8-disulphonic acid and the separation of 1-naphthylamine-4,8-disulphonic acid from the mother liquor is carried out at a temperature not higher than 70° C.

2. The process of claim 1, wherein the sulphonation mixture is introduced into water heated to at least 40° C.

3. The process of claim 1, wherein the water is initially introduced only partly as preheated water, and the remaining water is introduced at the same time as the sulphonation mixture.

4. The process of claim 1, wherein the concentration of sulphuric acid in the mother liquor of the suspension being produced after the introduction of the sulphonation mixture into the water initially introduced, is 10 to 70% by weight.

5. The process of claim 1, wherein the concentration of sulphuric acid in the mother liquor of the suspension being produced is 30 to 60% by weight.

6. The process of claim 1, wherein the separation of 1-naphthylamine-4,8-disulphonic acid from the mother liquor is carried out by filtration at 10° to 30° C.

7. The process of claim 1, wherein the sulphonation mixture used is obtained by the known sulphonation in sulphuric acid by introducing in turn $SO_3$, alkali metal sulphate and 1-naphthylamine-8-sulphonic acid while using a total of 1.5 to 3 mols of $SO_3$ and 0,6 to 1.5 mols of alkali metal sulphate per mole of 1-naphthylamine-8-sulphonic acid.

8. The process of claim 7, wherein a sulphonation mixture is used in the preparation of which 2.5 to 3 mols of $SO_3$ and 0.75 to 1 mol of alkali metal sulphate are employed per mol of 1-naphthylamine-8-sulphonic acid.

9. The process of claim 7, wherein in the preparation of the sulphonation mixture the sulphonation mixture is maintained at 10° to 40° C. during the addition of $SO_3$ and the subsequent reaction.

* * * * *